United States Patent [19]
Kolt

[11] Patent Number: 5,518,495
[45] Date of Patent: May 21, 1996

[54] MAGNETIC FIELD THERAPY APPARATUS

[75] Inventor: Stanley Kolt, Mamaroneck, N.Y.

[73] Assignee: Magnetherapy, Inc., Mamaroneck, N.Y.

[21] Appl. No.: 298,226

[22] Filed: Aug. 29, 1994

[51] Int. Cl.⁶ ................................................. A61N 1/00
[52] U.S. Cl. .................................................. 600/13; 600/15
[58] Field of Search ................................. 600/9–15

[56] References Cited

U.S. PATENT DOCUMENTS

| | | | |
|---|---|---|---|
| 3,658,051 | 4/1972 | MacLean | 128/1.5 |
| 3,915,151 | 10/1975 | Kraus | 600/13 |
| 4,177,796 | 12/1979 | Franco-Vila | 128/1.5 |
| 4,398,545 | 8/1983 | Wilson | 128/798 |
| 4,527,550 | 7/1985 | Ruggera et al. | 128/1.5 |
| 4,674,482 | 6/1987 | Waltonen et al. | 128/1.5 |
| 4,693,238 | 9/1987 | Jerabek | 128/1.5 |
| 4,758,429 | 7/1988 | Gordon | 424/85 |
| 4,765,310 | 8/1988 | Deagle et al. | 128/1.5 |
| 5,100,373 | 3/1992 | Liboff et al. | 600/13 |
| 5,131,904 | 7/1992 | Markoll | 600/14 |
| 5,181,902 | 1/1993 | Erickson et al. | 600/13 |

FOREIGN PATENT DOCUMENTS 6039042  2/1994  Japan ............................. 600/15

*Primary Examiner*—Angela D. Sykes
*Assistant Examiner*—John P. Lacyk
*Attorney, Agent, or Firm*—David L. Davis

[57] ABSTRACT

Apparatus for the treatment of arthritis utilizing magnetic field therapy includes an adjustable voltage source adapted to be connected to a source of line voltage and a coil connected to the adjustable voltage source. The coil is wound on a bobbin having a centrally disposed opening suitable for receiving therein appendages of a human being as well as body portions thereof. The bobbin is formed of copper or one of its alloys.

12 Claims, 3 Drawing Sheets

MAGNETIC FIELD THERAPY APPARATUS

BACKGROUND OF THE INVENTION

This invention relates to magnetic field therapy apparatus for treating joints afflicted with arthritis, bursitis or the like to reduce the painful symptoms associated therewith and, more particularly, to a portable alternating current electromagnetic field source adapted to receive portions of a living being therein.

The use of electromagnetic energy as a therapeutic aid for various types of joint diseases is documented in the art. For example, U.S. Pat. No. 5,131,904 to Markoll discloses an annular coil energized by a DC voltage wave pulsing at the rate of 1–30 cycles per second for applying the resulting magnetic field to the appendage of a human being afflicted with arthritis or bursitis.

U.S. Pat. No. 4,177,796 to Franco-Vila also relates to the application of pulsating electromagnetic energy in addition to thermal and vibrational energy to various parts of the body to help in curing the disease or at least giving relief to individuals who suffer pain from degenerative joint diseases. The device disclosed therein utilizes low frequency alternating current causing metallic fragments to vibrate and thus generate heat for thermal application to the body in conjunction with concentrated magnetic field energy and vibrations.

Among the shortcomings of the many devices known in the prior art is generally the fact that they are not portable and thus require the individual to appear at a doctor's or therapist's office since the patient is unable to utilize the equipment at home. In addition, the devices are rather complicated to operate and expensive to manufacture.

It is therefore a primary object of the present invention to overcome shortcomings found in the prior art by providing a lightweight portable apparatus that is reliable, inexpensive and suitable for the relief of pain due to degenerating joint diseases.

SUMMARY OF THE INVENTION

The foregoing and additional objects are attained in accordance with the principles of this invention by providing magnetic field therapy apparatus comprising a bobbin formed of non-magnetic material, the bobbin having a central opening adapted for receipt therein of at least an appendage of a living being, and a length of electrically conductive insulated wire wound around the bobbin to form a coil. Power means coupled to the length of wire energizes the coil with alternating current. The bobbin material is selected from the group consisting of copper and alloys thereof.

In accordance with an aspect of this invention, the bobbin material is brass.

In accordance with another aspect of this invention, the bobbin material is bronze.

In accordance with a further aspect of this invention, the power means is effective to produce a magnetic field within the bobbin central opening having a maximum flux density in the range of from about 4.5 gauss to about 6 gauss.

BRIEF DESCRIPTION OF THE DRAWINGS

The foregoing will be more readily apparent upon reading the following description in conjunction with the drawings in which like elements in different figures thereof are identified by the same reference numeral and wherein.

DETAILED DESCRIPTION

Figure 1:
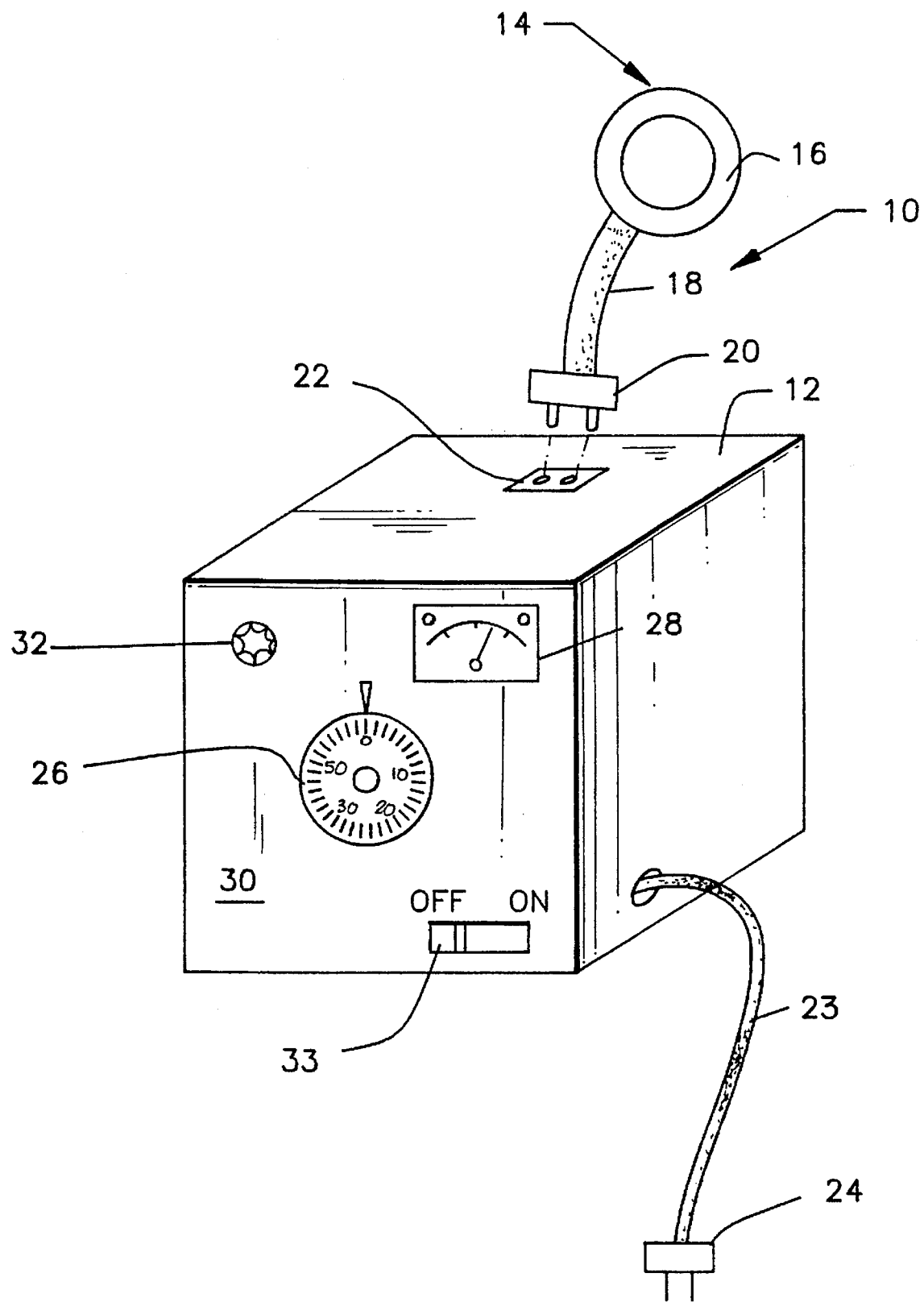
FIG. 1 is a perspective view schematically depicting apparatus constructed in accordance with the principles of this invention.

Referring to the drawings, FIG. 1 shows apparatus, designated generally by the reference numeral 10, constructed in accordance with the principles of this invention for providing magnetic field therapy for alleviating the painful symptoms of degenerative joint diseases such as arthritis, bursitis, and the like. The apparatus 10 includes a housing 12 containing circuitry connectable between a source of commercially available AC power and a magnetic field generator 14. As shown, the magnetic field generator 14, enclosed within an insulative toroidal housing 16, is connected to the circuitry within the housing 12 by means of a cable 18 terminated by a plug 20 adapted for receipt by a socket 22 mounted to the housing 12. The circuitry within the housing 12 is connected to commercially available AC power (i.e., at a standard wall outlet) by means of the cable 23 terminated by a standard wall outlet plug 24.

The front panel 30 of the housing 12 has mounted thereto an on/off switch 33, a control dial 26, a meter display 28 and an overcurrent protection device 32, such as a fuse or circuit breaker.

Figure 2:
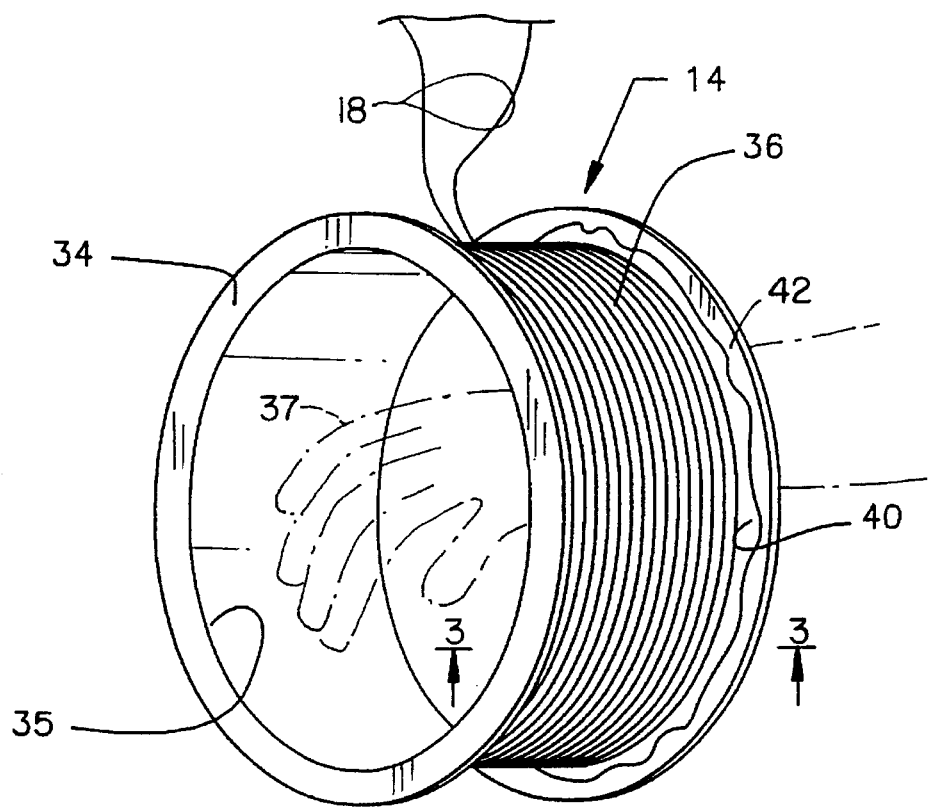
FIG. 2 is a perspective view of the bobbin and coil of this invention showing, in broken lines, an appendage of a living being received in the central opening of the bobbin.

FIG. 2 illustrates the magnetic field generator 14 without the housing 16. As shown, the magnetic field generator 14 includes a bobbin 34 formed of non-magnetic material. In accordance with the principles of this invention, the bobbin material is selected from the group consisting of copper and its alloys. Two such suitable alloys are brass (i.e., copper and zinc) and bronze (i.e., copper and tin). The bobbin 34 has a central opening 35 adapted to receive a portion of a living being therein. The body portion receivable within the opening 35 depends upon the size of the opening 35. For example, if the diameter of the opening 35 is on the order of six inches, this will accept a hand 37, as shown by the broken line representation thereof. If the opening 35 is large enough, it can surround a human torso.

The outer channel 42 of the bobbin 34 is lined with a sheet of cloth material 40, preferably linen. A length of electrically conductive insulated wire 36 is wound around the bobbin 34 over the cloth 36 and within the channel 42 so as to form a coil. The wire 36 is terminated in the cable 18 connected to the plug 20.

The size of the wire 36 and the number of turns forming the coil wound around the bobbin 34 is determined by the size of the bobbin 34 and the desire to keep heat generation from becoming excessive. In addition, the magnetic flux density of the magnetic field generated by the generator 14 is desired to be within a certain range, as will be discussed hereinafter.

Figure 3:
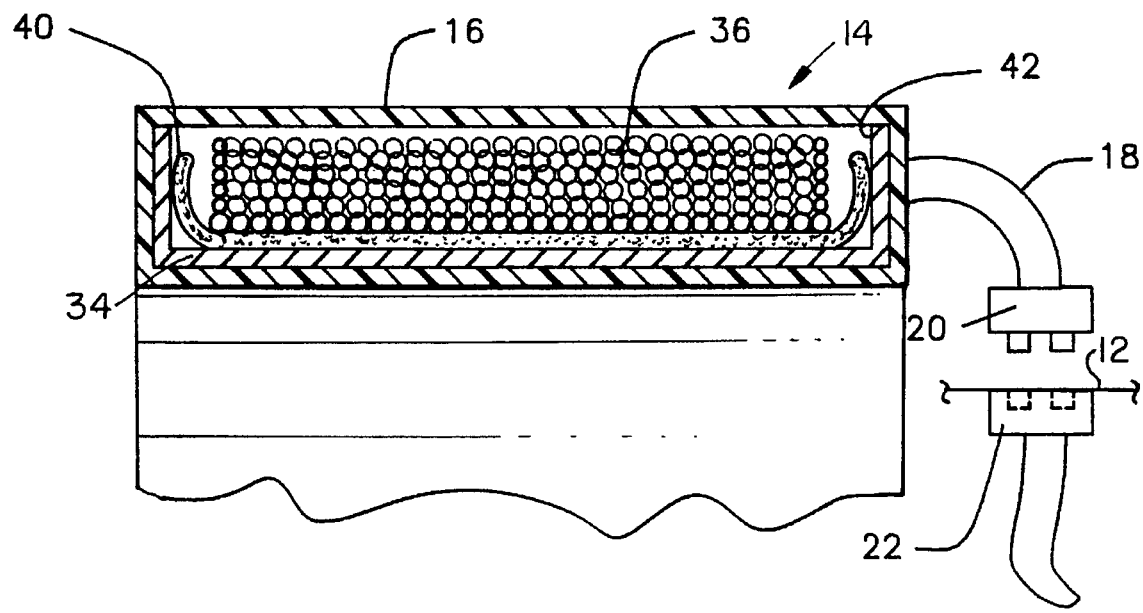
FIG. 3 is a cross sectional view taken along the line 3—3 in FIG. 2 and further showing a housing containing the bobbin and the coil.

As shown in FIG. 3, after the wire 36 is wound on the bobbin 34 to form a coil, an insulative toroidal housing, or cover, 16, preferably formed of a plastic material, is placed over the bobbin and coil to shield the wire 36 from the environment and prevent it from absorbing moisture, which might effect its operation.

Figure 4:
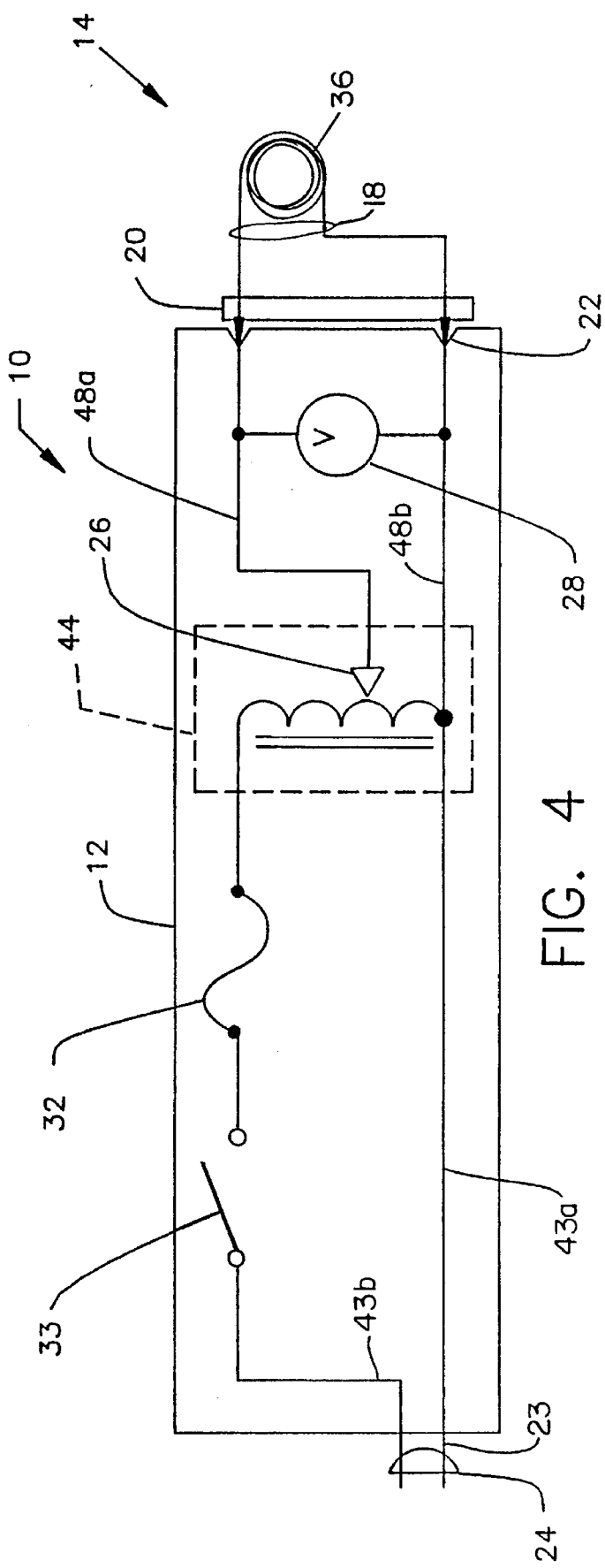
FIG. 4 is a circuit diagram showing illustrative circuitry for energizing the coil.

FIG. 4 shows illustrative circuitry contained within the housing 12 for controlling the generation of a magnetic field by the magnetic field generator 14. As shown, the plug 24 is a conventional wall plug adapted for insertion into a wall outlet connected to a source of commercially available AC power, illustratively, 120 volts at 60 Hertz. The plug 24 is connected by the cable 23 to the conductors 43*a*, 43*b* within the housing 12 and thereby to the input of the voltage adjuster 44. In series with the conductor 43*b* is the on/off switch 33 and the overcurrent protection device 32. Illustratively, the voltage adjuster 44 comprises an autotransformer whose movable secondary tap is part of the control dial 26 mounted to the front panel 30 of the housing 12. The output of the voltage adjuster 44 on the conductors 48*a*, 48*b* is connected to the socket 22. The voltmeter 28, whose display is visible through the front panel 30 of the housing 12, is connected across the conductors 48*a*, 48*b*. The plug 20 of the magnetic field generator 14 is insertable into the socket 22 to complete the circuit.

Figure 5:
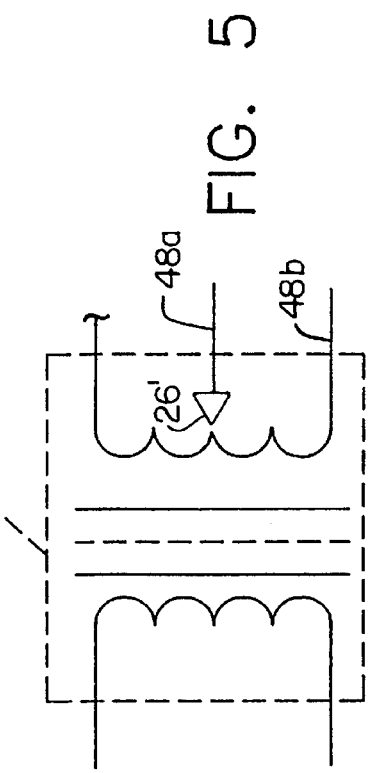
FIG. 5 shows a modification to a portion of the circuitry of FIG. 4.

An alternative construction for the voltage adjuster 44 is shown in FIG. 5 and designated by the reference numeral 44'. In this alternative construction, the voltage adjuster 44' is a step down transformer having a variable tap 26' on its secondary winding, which is connected to the output conductors 48*a*, 48*b*. The arrangement shown in FIG. 5 isolates the magnetic field generator 14 from the input plug 24 to provide further protection to the user of the device.

By applying alternating current to the wire 36 forming the coil of the magnetic field generator 14, a magnetic field is generated within the central opening 35 of the bobbin 34. This field is strongest at the outer periphery of the opening 35 and decreases toward its center. It has been found that a maximum magnetic flux density in the range of from about 4.5 gauss to about 6 gauss is most effective. To achieve that field, an output voltage from the voltage adjuster 44 is in the range from about 6 volts to about 50 volts. It is understood that the number of turns of the wire 36 forming the coil is a factor in the strength of the magnetic field. Experiments with various materials for the bobbin 34 resulted in a selection of copper or its alloys as the material of choice. Such alloys include brass and bronze. It is believed that the copper, brass or bronze bobbin, through the eddy currents induced therein by the varying magnetic field, has a filter effect on the magnetic field which promotes the therapeutic benefits produced by the inventive apparatus.

Accordingly, there has been disclosed an improved magnetic field therapy apparatus for treating joints afflicted with arthritis, bursitis or the like. While illustrative embodiments of the present invention have been disclosed herein, it is understood that various modifications and adaptations to the disclosed embodiments will be apparent to those of ordinary skill in the art and it is intended that this invention be limited only by the scope of the appended claims.

What is claimed is:

1. Magnetic field therapy apparatus comprising:

a bobbin formed of non-magnetic material, said bobbin having a central opening adapted for receipt therein of at least an appendage of a living being;

a length of electrically conductive insulated wire wound around said bobbin to form a coil; and power means coupled to said length of wire for energizing said coil with alternating current;

wherein said bobbin material is selected from the group consisting of copper and alloys thereof.

2. The apparatus according to claim 1 wherein said bobbin material comprises brass.

3. The apparatus according to claim 1 wherein said bobbin material comprises bronze.

4. The apparatus according to claim 1 wherein said power means is effective to produce a magnetic field within said bobbin central opening having a maximum flux density in the range of from about 4.5 gauss to about 6 gauss.

5. The apparatus according to claim 1 wherein said power means includes adjustment means for varying the current applied to said coil.

6. The apparatus according to claim 5 wherein said power means is adapted for connection between a source of commercially available AC power and said coil, and said adjustment means includes a variable transformer.

7. The apparatus according to claim 6 wherein said transformer is an autotransformer having a movable secondary tap.

8. The apparatus according to claim 6 wherein said transformer is a step down transformer having a secondary winding with a variable tap.

9. The apparatus according to claim 5 further including metering means coupled to said adjustment means for providing an indication of the power applied to said coil.

10. The apparatus according to claim 1 further including a layer of cloth interposed between said bobbin and said coil.

11. The apparatus according to claim 10 wherein said cloth is linen.

12. The apparatus according to claim 1 further including an electrically insulative toroidal housing enclosing said bobbin and said coil.

\* \* \* \* \*